(12) United States Patent
Goshayeshgar (10) Patent No.: US 9,861,431 B2
(45) Date of Patent: Jan. 9, 2018

(54) RADIOFREQUENCY INFLATABLE DEVICE

(71) Applicant: KYPHON SARL, Neuchatel (CH)

(72) Inventor: Mojan Goshayeshgar, Atherton, CA (US)

(73) Assignee: Kyphon SÀRL, Neuchâtel (CH)

( * ) Notice: Subject to any disclaimer, the term of this patent is extended or adjusted under 35 U.S.C. 154(b) by 225 days.

(21) Appl. No.: 13/799,200

(22) Filed: Mar. 13, 2013

(65) Prior Publication Data

US 2014/0276724 A1 Sep. 18, 2014

(51) Int. Cl.
*A61B 18/18* (2006.01)
*A61B 18/14* (2006.01)
*A61B 18/00* (2006.01)
*A61B 17/22* (2006.01)
*A61B 17/88* (2006.01)

(52) U.S. Cl.
CPC ...... *A61B 18/1492* (2013.01); *A61B 17/8836* (2013.01); *A61B 2017/22051* (2013.01); *A61B 2018/0022* (2013.01); *A61B 2018/00023* (2013.01); *A61B 2018/0044* (2013.01); *A61B 2018/00267* (2013.01); *A61B 2018/00285* (2013.01)

(58) Field of Classification Search
CPC ........ A61B 18/1492; A61B 2018/0022; A61B 2018/00267; A61B 17/8836; A61B 2017/22051; A61B 2018/00285; A61M 2025/1086; A61M 25/1002; A61M 29/02
USPC .................................................. 606/27, 192
See application file for complete search history.

(56) References Cited

U.S. PATENT DOCUMENTS

| | | | |
|---|---|---|---|
| 5,536,267 A | 7/1996 | Edwards | |
| 6,004,269 A | 12/1999 | Crowley et al. | |
| 6,056,744 A | 5/2000 | Edwards | |
| 6,254,598 B1 * | 7/2001 | Edwards | A61B 18/1206 606/41 |
| 6,322,560 B1 | 11/2001 | Garbagnati et al. | |
| 6,506,189 B1 * | 1/2003 | Rittman, III | A61B 18/1482 606/41 |
| 6,780,183 B2 | 8/2004 | Jimenez et al. | |
| 7,184,811 B2 | 2/2007 | Phan | |
| 7,371,232 B2 | 5/2008 | Scheib | |
| 7,959,631 B2 | 6/2011 | DiCarlo | |
| 8,192,442 B2 | 6/2012 | Truckai et al. | |
| 8,388,573 B1 * | 3/2013 | Cox | A61M 25/1002 604/103.01 |
| 9,173,701 B2 | 11/2015 | Goshayeshgar | |
| 2001/0034518 A1 | 10/2001 | Edwards et al. | |

(Continued)

FOREIGN PATENT DOCUMENTS

WO 2012122157 A1 9/2012

OTHER PUBLICATIONS

International Search Report and Written Opinion for PCT/US2014/022452, the counterpart application dated Jul. 15, 2014.

*Primary Examiner* — Lindsey G Wehrheim (57) ABSTRACT

A device for performing a surgical procedure comprises an elongated shaft extending between a proximal end and a distal end and defines an outer surface and an inner surface. An expandable member is disposed at the distal end and is configured to receive inflation material. At least one electrode is disposed with the inflatable member. A cooling mechanism is configured to cool surrounding tissue that the device comes in contact.

13 Claims, 4 Drawing Sheets

(56) References Cited

U.S. PATENT DOCUMENTS

| | | |
|---|---|---|
| 2003/0163126 A1 | 8/2003 | West |
| 2003/0236455 A1 | 12/2003 | Swanson et al. |
| 2004/0167509 A1* | 8/2004 | Taimisto ............ A61B 18/1492 606/41 |
| 2005/0096647 A1 | 5/2005 | Steinke et al. |
| 2005/0288730 A1* | 12/2005 | Deem et al. .................... 607/42 |
| 2006/0122614 A1 | 6/2006 | Truckai et al. |
| 2007/0129720 A1* | 6/2007 | Demarais et al. .............. 606/41 |
| 2012/0022574 A1 | 1/2012 | Mafi et al. |
| 2012/0029509 A1 | 2/2012 | Smith |
| 2012/0029511 A1 | 2/2012 | Smith et al. |
| 2012/0053611 A1 | 3/2012 | Saab et al. |
| 2012/0090156 A1 | 7/2012 | Ballon |
| 2013/0296855 A1 | 11/2013 | Sigmon, Jr. |
| 2014/0031810 A1 | 1/2014 | Mahvi |
| 2014/0236144 A1 | 8/2014 | Krueger et al. |
| 2014/0276728 A1 | 9/2014 | Goshayeshgar |

\* cited by examiner

RADIOFREQUENCY INFLATABLE DEVICE

TECHNICAL FIELD

The present disclosure generally relates to medical devices for the treatment of soft tissue and/or nerves. More particularly, the present disclosure relates to a surgical system and method of employing an inflatable device in soft tissue so as to achieve a uniform (impedance) and larger contact area so for nerve destruction.

BACKGROUND

Rhizotomy is a term referring to a neurosurgical procedure that selectively destroys problematic nerve roots in the spinal cord, most often to relieve the symptoms of neuromuscular conditions such as spastic diplegia and other forms of spastic cerebral palsy. The selective dorsal rhizotomy (SDR) for spastic cerebral palsy has been the main use of rhizotomy for neurosurgeons specializing in spastic CP since the 1980s; in this surgery, the spasticity-causing nerves are isolated and then targeted and destroyed. The sensory nerve roots, where spasticity is located, are first separated from the motor ones, and the nerve fibers to be cut are then identified via electromyographic stimulation. The ones producing spasticity are then selectively lesioned with tiny electrical pulses.

In spasticity, rhizotomy precisely targets and destroys the damaged nerves that don't receive gamma amino butyric acid, which is the core problem for people with spastic cerebral palsy. These over-firing, non-GABA-absorbing nerves generate unusual electrical activity during the EMG testing phase in SDR and are thus considered to be the source of the patient's hypertonia; they are eliminated with the electrical pulses once identified, while the remaining nerves and nerve routes carrying the correct messages remain fully intact and untouched. This means that the spasticity is permanently dissolved, and that this is done without affecting nervous system sensitivity or function in other areas, because the only nerves destroyed are the over-firing ones responsible for the muscle tightness.

The terms rhizotomy and neurotomy are also increasingly becoming interchangeable in the treatment of chronic back pain from degenerative disc disease. This is a procedure called a facet rhizotomy and is not a surgical procedure but is instead done on an outpatient basis using a simple probe to apply radiofrequency waves to the impinged pain-causing nerve root lying between the facet joint and the vertebral body. Such radio frequency nerve lesioning results in five to eight or more months of pain relief before the nerve regenerates and another round of the procedure needs to be performed. A facet rhizotomy is just one of many different forms of radiofrequency ablation, and its use of the "rhizotomy" name should not be confused with the SDR procedure.

SUMMARY

Accordingly, this application is directed to a device for performing a surgical procedure in accordance with the principles of this disclosure. The system comprises an elongated shaft extending between a proximal end and a distal end and defining an outer surface and an inner surface. An expandable member is disposed at the distal end and is configured to receive inflation material. At least one electrode is disposed with the inflatable member. A cooling mechanism is configured to cool the inflation material so as to cool the tissue that the balloon comes in contact. Cooling the tissue will in turn increase the depth of the lesion. The larger the lesion increases the duration of pain relief and the efficacy of the treatment.

In one embodiment, a device for performing a surgical procedure comprises a cannula extending between a proximal end and a distal end and defines an outer surface and an inner surface. A balloon is disposed at the distal end and is configured to receive inflation material and including an inner surface defining a cavity. At least one electrode is disposed with the balloon. A cooling tube is disposed within the cavity of the balloon and is configured to attach to a liquid pumping device to circulate cooled liquid within the cooling tube so as to cool the inflation material.

In one embodiment, a method for destroying nerves at a surgical site is provided. The method comprises providing a device in accordance with the principles of this disclosure. An access path is created to the surgical site. A balloon is inserted into the surgical site and inflated. RF signals are emitted through the electrodes to destroy nerves at the surgical site.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

The exemplary embodiments of the surgical system and related methods of use disclosed are discussed in terms of medical devices for the treatment of musculoskeletal disorders and more particularly, in terms of a surgical system and method for nerve destruction.

Radiofrequency (RF) ablation devices have been available to surgeons to treat many medical conditions, for example, in the treatment of tumors in lung, liver, kidney, bone and other body organs. Pulsed RF has also been used for treatment of tumors, cardiac arrhythmias, chronic and post-operative pain, bone fracture and soft tissue wounds.

Minimally invasive procedures in nerve and/or soft tissue such as the spine or the breast, however, are difficult to perform using standard scissors and scalpel. Furthermore, in a closed environment, radio frequency current dissipates into the surrounding tissue causing a decreased ability to achieve a current at the cutting electrode of sufficiently high density to initiate a cut. To overcome this problem, high power settings are often required to initiate the cut which often is painful and increases thermal damage to the tissue whether using a standard or a custom electrosurgical generator.

Another problem associated with cutting tissue is the control of bleeding. Radio frequency energy controls bleeding by coagulating small blood vessels. Another method of controlling bleeding is through the use of heat. For example, some commercially available scalpels use direct heat to control bleeding. However, while the bleeding is generally controlled, the cutting of tissue is often slower than with radio frequency energy and the knife edge readily dulls. Other commercially available scalpels use ultrasonic energy generally at 50 kHz to heat the tissue so as to coagulate severed blood vessels but cut slower than a standard electrosurgical electrode and are costly as a custom ultrasonic generator is required.

Facet Rhizotomy aims at destroying the nerves in the facet joint to eliminate pain sensation. Rhizotomy usually uses radio frequency energy to temporarily interrupt or destroy the medial branch nerves. In one embodiment, a cooled RF balloon catheter to create a larger volume lesion to ablate the targeted nerves and alleviate a chronic facet-mediated pain is provided.

In one embodiment, the balloon has one or multiple RF electrodes. The electrode(s) can be straight, helical, curved symmetrical, or asymmetrical and positioned symmetrically or directionally. The electrode(s) can be disposed inside, outside or within the wall thickness of the balloon. The electrodes are deployed with the balloon. To cool the system, a liquid pumping system also may be connected to the balloon to inflate and cool down the inflation liquid dynamically (active cooling) or the balloon may be inflated with a cooled liquid (passive cooling).

In one embodiment, the device is advanced to the target lesion location under fluoroscopic guidance. Catheter placement will be confirmed under fluoroscopy. The balloon will be inflated to its formed volume. The RF will be applied after initial inflation of the balloon. The active or passive cooling of the balloon creates a large elliptical lesion in the geometry of the balloon, so as to overcome the variability of the medial branch nerve course, thus more effective disruption of the pain signals.

It is contemplated that one or all the components of the surgical system may be disposable, peel-pack, pre-packed sterile devices. In various embodiments, one or all the components of the surgical system may be reusable. Further, the surgical system may be configured as a kit with multiple sized and configured components, such as, for example, inflatable members that are preformed to have different sizes and/or shapes.

It is envisioned that the present disclosure may be employed to treat bones, in particular, arm bones such as a distal radius. It should be understood that the present principles are applicable to any bone structures, including but not limited to bones of the spine, legs, feet, arms, etc. It is contemplated that the present disclosure may be employed with other osteal and bone related applications, including those associated with diagnostics and therapeutics. It is further contemplated that the disclosed surgical system and methods may alternatively be employed in a surgical treatment with a patient in a prone or supine position, and/or employ various surgical approaches, including anterior, posterior, posterior mid-line, direct lateral, postero-lateral, antero-lateral, etc. approaches in the calcaneus, spine or other body regions. The present disclosure may also be alternatively employed with procedures for treating the muscles, ligaments, tendons or any other body part. The system and methods of the present disclosure may also be used on animals, bone models and other non-living substrates, such as, for example, in training, testing, and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure.

As used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The components of system 10 can be fabricated from biologically acceptable materials suitable for medical applications, including metals, synthetic polymers, ceramics and bone material and/or their composites, depending on the particular application and/or preference of a medical practitioner. For example, the components of system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference.

The components of system 10, individually or collectively, may also be fabricated from a heterogeneous material such as a combination of two or more of the above-described materials. The components of system 10 may be monolithically formed, integrally connected or include fastening elements and/or instruments, as described herein.

The following discussion includes a description of a system for performing a surgical procedure and related methods of employing the system in accordance with the principles of the present disclosure. Alternate embodiments are also disclosed. Reference will now be made in detail to the exemplary embodiments of the present disclosure, which are illustrated in the accompanying figures. Turning now to FIGS. 1-4, there are illustrated components of the system for performing a surgical procedure in accordance with the principles of the present disclosure.

Figure 1:
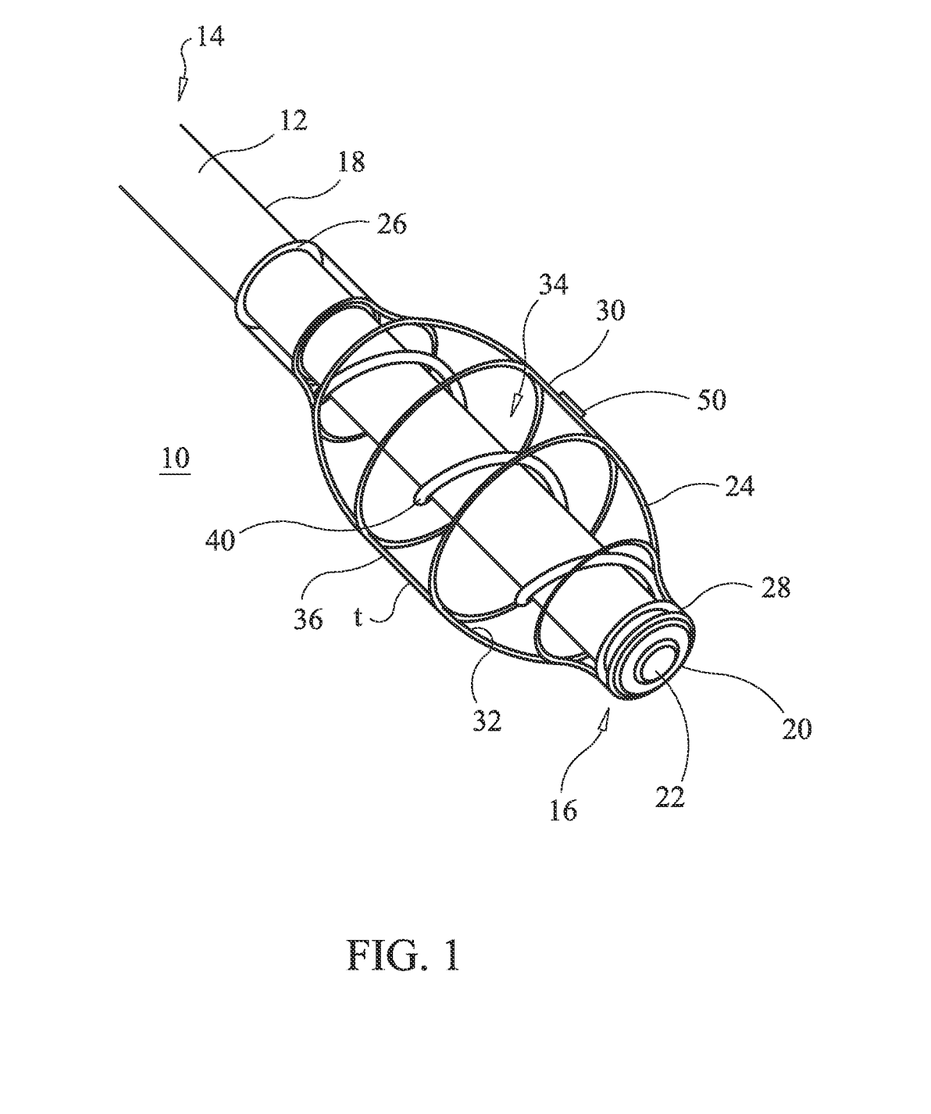
FIG. 1 is a perspective view, with partial cross section, of one embodiment of a surgical system in accordance with the principles of the present disclosure.
Figure 2:
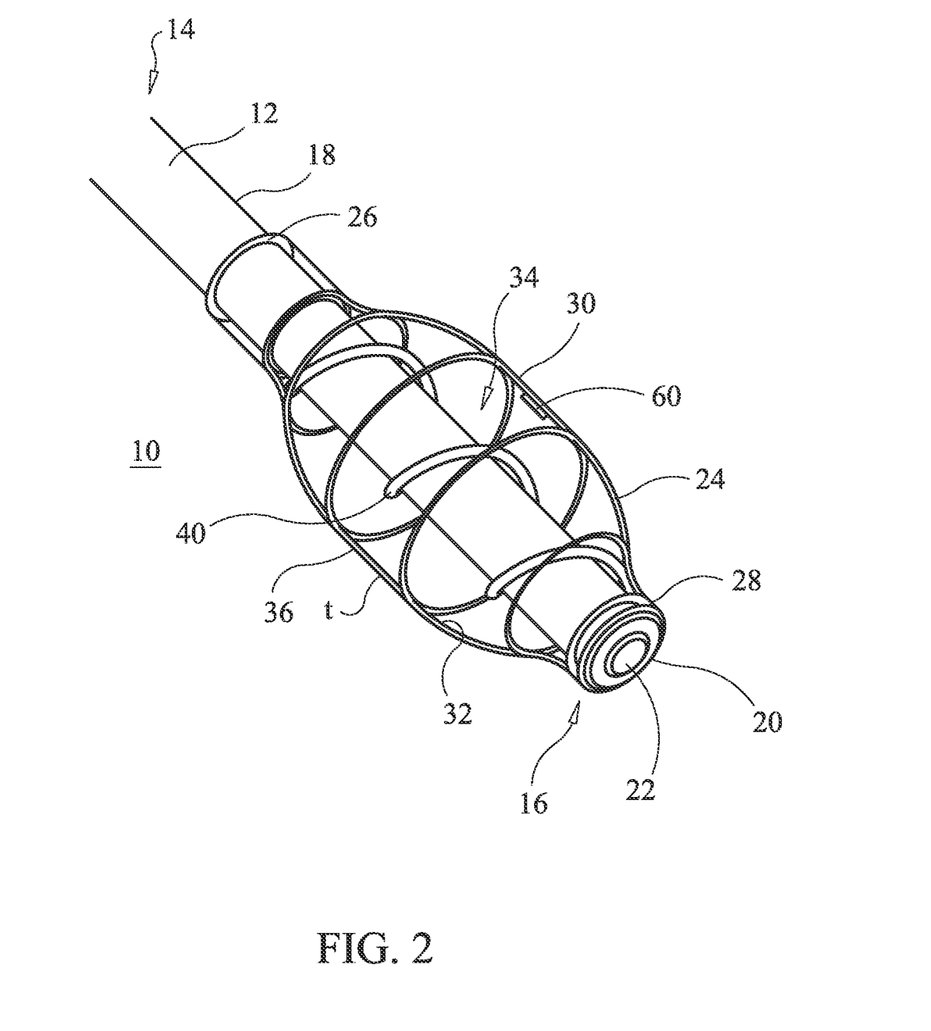
FIG. 2 is a perspective view, with partial cross section, of one embodiment of a surgical system in accordance with the principles of the present disclosure.
Figure 3:
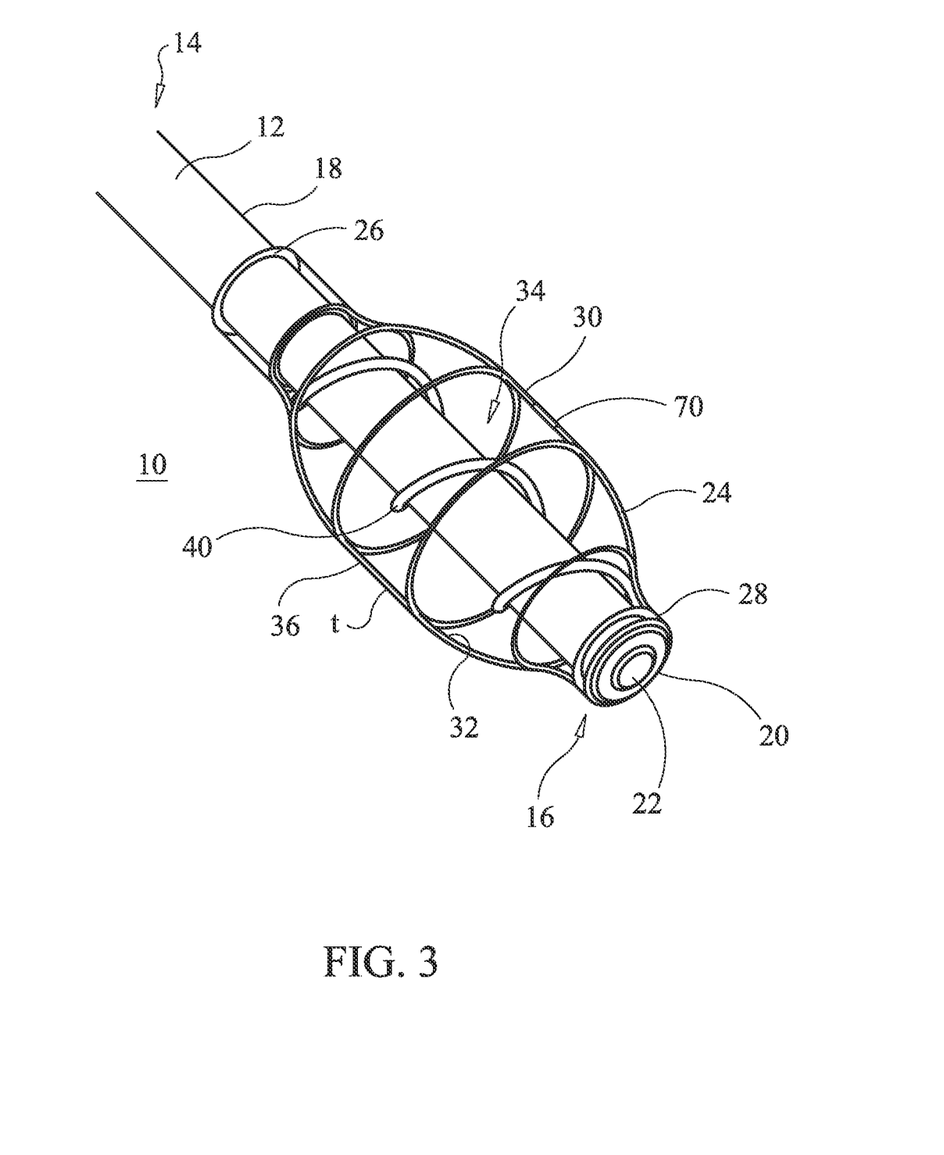
FIG. 3 is a perspective view, with partial cross section, of one embodiment of a surgical system in accordance with the principles of the present disclosure.

As shown in FIGS. 1-3, balloon system 10 includes an elongated shaft 12. Shaft 12 extends between a proximal end 14 and a distal end 16. Shaft 12 includes an outer surface 18 and an inner surface 20. Surface 20 defines a passageway 22. Passageway 22 extends the entire length of shaft 12 and has a cylindrical cross sectional configuration having a uniform diameter along the length of passageway 22. In some embodiments, passageway 22 may have alternate cross section configurations, such as, for example, oval, oblong, triangular, square, hexagonal, polygonal, irregular, uniform, non-uniform and/or tapered.

An inflatable member, such as, for example, a balloon 24 is disposed with distal end of shaft 12. Balloon 24 has a proximal end 26 and a distal end 28. Balloon 24 includes an outer surface 30 and an inner surface 32. Surface 32 defines a cavity 34 extending the entire length of balloon 24. Balloon 24 includes a wall 36 extending between surfaces 30 and 32 and defines a thickness t. Shaft 12 may be attached to a fill tube (not shown) such that a material, such as, for example, saline, a contrast solution or compressed air may be delivered from the tube, through passageway 22 and into cavity 34. As the material fills cavity 34, balloon moves from an unexpanded configuration to an expanded configuration. It is envisioned that the shapes and sizes of balloon 24 when in the expanded configuration can be selected to provide a desired result during a procedure. For example, balloon 24 may include shapes such as spheres, cylinders, etc. and have different dimensions to make balloon 24 narrower or wider in a longitudinal direction, or extend further in a radial direction. Balloon 24 may be configured to expand outward in all directions from cavity 34 or alternatively be configured to expand in only one direction from cavity 34 such that cavity 34 is compliant with a predetermined form. Balloon 24 comprises a compliant material, such as, for example, polyurethane, pellethane, polyethylene, silicone, cronoprene or non-compliant material such as Nylon.

It is envisioned that balloon 24 can be a single or multi-layered balloon where each balloon layer has the same diameter and/or wall thickness, is comprised of the same material or materials having substantially identical mechanical properties, and has the same degree of molecular orientation in the body portion of the balloon. It will be apparent that in some situations it will be desirable to have some balloon layers having different thicknesses, materials, and/or degree of molecular orientations upon deflation, while at the same time having equivalent size, mechanical properties, and/or orientation upon inflation or expansion. For other applications, it will be apparent that one can vary size, material, and/or orientation to at least some degree, depending upon the requirements of a particular application.

In one embodiment of the present disclosure an inflatable device is provided as further described below. The inflatable device comprises an inflatable balloon attached to a catheter that is inflated in soft tissue. By inflating the balloon in soft tissue a uniform (impedance) and larger contact area is created. A uniform and larger contact area may increase the depth of the lesion and overcome the variability of positioning the probe to target the particular nerve, for example, to target the facet medial branch nerves.

It is contemplated that balloon 24 may include an impenetrable structural layer having low friction surfaces so as to facilitate deployment through a delivery tube, such as, for example, through shaft 12 and prevent rupture of balloon 24 as it is inflated or expanded in situ. Further variations are contemplated involving different combinations of lubricating layers and structural layers. In some embodiments, structural layers of balloon 24 contain polyamides, polyesters, polyethylenes, polyurethanes, their co-polymers and/or combinations thereof.

At least one electrode 50 is disposed with balloon 24. Electrode 50 is configured to emit an RF frequency for cutting and/or destroying tissue or nerves, In one embodiment, as shown in FIG. 1, electrode 50, is disposed on outer surface 30. In one embodiment, as shown in FIG. 2, electrode 60 is disposed on inner surface 32. In one embodiment, as shown in FIG. 3, electrode 70 is disposed within wall 36. Each of the specific constructs of the present disclosure requires an entirely different material and manufacturing process. The control mechanism, temperature verses impedance or energy is a function of the particular tissue type in which it is being deployed and the nature of the electrode contact. The present disclosure provides varying configurations each providing particular advantages for particular tissue types or nerves that the construct is to be used. One skilled in the art would choose the particular construct based on the tissue, type, location, nerve as well as other parameters of the procedure in which the device of the present disclosure is to be used. Electrode 50 can be of any shape such as, for example, straight, helical, curved symmetrical, or asymmetrical and positioned symmetrically or directionally if more than one electrode 50 is provided, they can be positioned symmetrically or directionally along balloon 24. Other constructs and designs of the electrodes can be used and are understood to fall within the present disclosure. It is understood by one skilled in the art that the RF signal used is configured to temporarily interrupt or destroy nerves to reduce pain in the patient.

A cooling mechanism is provided and is configured to cool inflation material in balloon 24. In one embodiment, as shown in FIG. 1, active cooling is providing by the cooling mechanism including a cooling tube 40 disposed in within cavity 34 that extends through shaft 12 and is connected to a liquid pumping system (not shown). In one embodiment, cooling tube 40 is disposed within wall 36 of balloon 24. In one embodiment, cooling tube 40 spirals around shaft 12 so as to facilitate uniform cooling of the inflatable material. In one embodiment, passive cooling is provided by cooling the inflation material prior to filling balloon 24.

In some embodiments, shaft 12 and/or balloon 24 includes one or a plurality of marker bands (not shown) comprising a radiopaque material. In one embodiment, the polymeric material is polyether block amide. In some embodiments, the highly radiopaque material incorporated into the polymeric material is barium sulfate, bismuth subcarbonate, tungsten, or a combination thereof. In one embodiment, the radiopaque markers are oppositely positioned strips of radiopaque markers as would be seen through x-ray imaging, such that the strips of radiopaque markers would be superimposed in the image. Balloon 24 is rotated in either clockwise or counter-clockwise repeatedly and in smaller increments of rotation until the x-ray image displays the radio-opaque strips in a desired orientation, which may be determined before the procedure by a medical practitioner.

In assembly, operation and use, system 10 is employed with a surgical procedure, such as, a facet rhizotomy procedure. It is contemplated that one or all of the components of system 10 can be delivered or implanted as a preassembled device or can be assembled in situ. System 10 may be completely or partially revised, removed or replaced. It is envisioned that system 10 may also be used to treat other affected portions of the patient, such as, for example, a calcaneus bone, bones of the feet or hands, bones of the spine, bones of the arms and legs, etc.

In use, to treat a damaged nerve, a medical practitioner obtains access to a surgical site in any appropriate manner, such as through incision and retraction of tissues. In one embodiment, a drill is employed to remove bone tissue to provide access to a repair site. It is envisioned that system 10 can be used in any existing surgical method or technique including open surgery, mini-open surgery, minimally invasive surgery and percutaneous surgical implantation, whereby the fractured or injured bone is accessed through a mini-incision or sleeve that provides a protected passageway to the area. Once access to the surgical site is obtained, the particular surgical procedure can be performed for treating the injury or disorder. The configuration and dimension of system 10 is determined according to the configuration, dimension and location of a selected section of nerves and the requirements of a particular application.

An incision is made in the body of a patient and a cutting instrument, such as a cannula or other device, creates a surgical pathway for implantation of components of system 10. A preparation instrument (not shown) can be employed to prepare tissue surfaces, as well as for aspiration and irrigation of a surgical region according to the requirements of a particular surgical application.

Balloon 24 is inserted through a cannula and inflated with an inflation material, such as saline or inert gas. In one embodiment, inflation material is delivered via a single gas source with a manifold and independently controlled valves such that the valves may be employed in controlled pressurized flow to balloon 24. It will be understood by those skilled in the art that any other suitable methods of inflation may be utilized.

A material, such as, for example, saline, a contrast solution or compressed air may be delivered through shaft 12 and passageway 22 and into cavity 34. The material may be delivered into cavity 34 until balloon 24 assumes the desire profile. Balloon 24 can he manipulated to the desired location by viewing balloon 24 with use of markers, Once bailoon 24 is properly positioned, electrode(s) 50 can be activated to emit the desire RF signal to temporarily interrupt or destroy nerves. RF signals may increase the temperature of balloon 24, therefore the cooling mechanism is utilized to decrease the temperature so that the procedure can be repeated at various locations. Removal of the material from cavity 34 causes balloon 24 to move from the expanded configuration to the unexpanded for removal from the patient.

Figure 4:
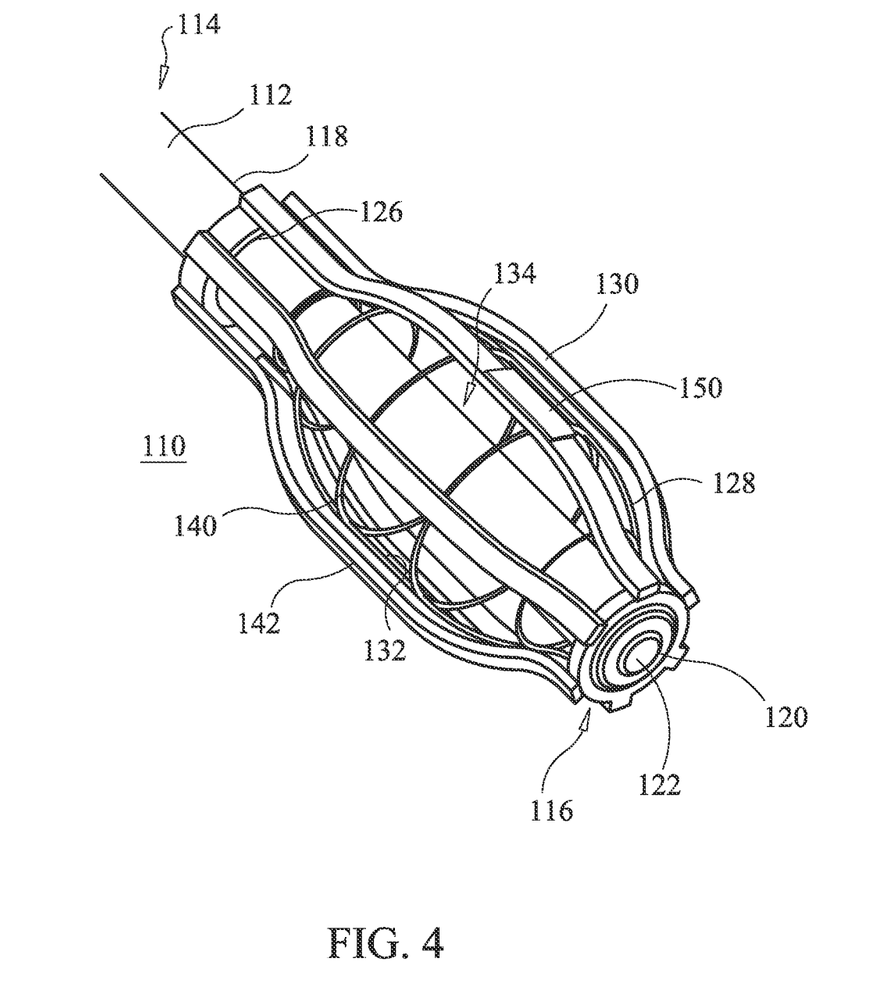
FIG. 4 is a perspective view, with partial cross section, of one embodiment of a surgical system in accordance with the principles of the present disclosure.

As shown in FIG. 4, balloon system 110 includes an elongated shaft 112. Shaft 112 extends between a proximal end 114 and a distal end 116. Shaft 112 includes an outer surface 118 and an inner surface 120. Surface 120 defines a passageway 122. A balloon 124 is provided at distal end 116 of shaft 12. Balloon 124 has a proximal end 126 and a distal end 128. Balloon 124 includes an outer surface 130 and an inner surface 132. Surface 132 defines a cavity 134 extending the entire length of balloon 124. Cavity 134 is configured to receive an inflation material.

An expandable cage 142 is disposed around balloon 124. Cage 142 provides a certain amount of stiffness to balloon 124 and protects balloon from boney material that may puncture balloon 124. In one embodiment, electrode 150 is disposed with cage 142. The cage configuration provides a robust and accurate control of RF energy deposition. Another benefit of using the cage as described throughout the present disclosure is the ease of manufacturing. Cage 142 is configured to expand with balloon 124 as surface 130 of balloon 124 applies force to cage 142. As discussed above, a cooling mechanism, such as, for example, cooling tube 140 is provided and is configured to cool inflation material in balloon 124.

In some embodiments, shaft 12 and/or balloon 24 includes one or a plurality of marker bands (not shown) comprising a radiopaque material. In one embodiment, the polymeric material is polyether block amide. In some embodiments, the highly radiopaque material incorporated into the polymeric material is barium sulfate, bismuth subcarbonate, tungsten, or a combination thereof. In one embodiment, the radiopaque markers are oppositely positioned strips of radiopaque markers as would be seen through x-ray imaging, such that the strips of radiopaque markers would be superimposed in the image. Balloon 24 is rotated in either clockwise or counter-clockwise repeatedly and in smaller increments of rotation until the x-ray image displays the radio-opaque strips in a desired orientation, which may be determined before the procedure by a medical practitioner.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto. The balloon can be modified or extended to accommodate particular formulations of balloon construction materials or fabrication techniques. Different balloon materials and surface coatings, or outer layers of different materials or surface coatings may also be applied to the balloon to facilitate a smaller balloon profile, biocompatibility, lubrication as well as other properties. The embodiments above can also be modified so that some features of one embodiment are used with the features of another embodiment. One skilled in the art may find variations of these preferred embodiments, which, nevertheless, fall within the spirit of the present invention, whose scope is defined by the claims set forth below.

What is claimed is:

1. A device for performing a surgical procedure comprising:
    an elongated shaft extending between a proximal end and a distal end, the elongated shaft including an outer surface, an inner surface, and an expandable member having an unexpanded position and an expanded position disposed at the distal end, the expandable member including at least a wall, the wall of the expandable member defining a thickness, an outer surface and an inner surface, the inner surface of the expandable member defining a cavity, the cavity configured to receive an inflation material, the elongated shaft and the expandable member defining a central longitudinal axis;
    at least a first electrode disposed on the inner surface of the expandable member;
    a cooling mechanism, the cooling mechanism including a cooling tube within the thickness of the wall, the cooling tube being configured to cool the inflation material, thereby cooling surrounding tissue with which the device comes into contact; and
    an expandable cage disposed around the expandable member, the expandable cage including at least a first elongated member, a second elongated member, and a collar adjacent proximal ends of the first and second elongated members, the first and second elongated members being spaced entirely apart from one another via a gap in the expandable cage, the first elongated member having a first length and the second elongated member having a second length, the central longitudinal axis lying in a first plane that extends through the first elongated member along the first length, and the central longitudinal axis lying in a second plane that extends through the second elongated member along the second length, the first and second elongated members each including an outer surface, an inner surface, and two side surfaces extending between the outer and inner surfaces, the outer surface, the inner surface, and the two side surfaces each having a minimum dimension transverse to the central longitudinal axis, the minimum dimensions of the outer and inner surfaces being at least two times greater than the minimum dimensions of the side surfaces, and the outer and inner surfaces each having a length and including flattened portions along majorities of the lengths thereof, the expandable cage being configured to expand with the expandable member in a direction transverse to the central longitudinal axis when the outer surface of the expandable member, during expansion of the expandable member to the expanded position, applies a force to the inner surfaces of the first and second elongated members.

2. A device as recited in claim 1, further comprising at least a second electrode disposed within the thickness of the wall.

3. A device as recited in claim 1, further comprising at least a second electrode disposed on the outer surface of the expandable member.

4. A device as recited in claim 1, wherein the cooling tube is in communication with a liquid pumping system.

5. A device as recited in claim 1, wherein the cooling mechanism further includes a liquid pumping system configured to cool the inflation material as the inflation material is pumped into the expandable member through the elongated shaft.

6. A device as recited in claim 1, wherein the at least the first electrode is configured to destroy one of tissue and nerves.

7. A device as recited in claim 6, wherein the at least the first electrode is configured to emit an RF signal to destroy the one of tissue and nerves.

8. A device as recited in claim 1, wherein the at least the first electrode is configured to be one of straight, helical, curved, symmetrical, asymmetrical, directional, and a combination thereof.

9. A device as recited in claim 1, further comprising at least a second electrode disposed on an outer surface of the cage.

10. A device for performing a surgical procedure comprising:
    a cannula extending between a proximal end and a distal end, the cannula including an outer surface and an inner surface;
    a balloon having an unexpanded position and an expanded position disposed at the distal end, the balloon configured to receive an inflation material, and including at least a wall, the wall of the balloon defining a thickness, an outer surface and an inner surface, the inner surface of the balloon defining a cavity, the cannula and the balloon defining a central longitudinal axis;
    at least a first electrode disposed on the inner surface of the balloon;
    a cooling tube disposed within the thickness of the wall, the cooling tube being configured to attach to a liquid pumping device, and to circulate cooled liquid within the cooling tube, so as to cool the inflation material, thereby cooling surrounding tissue with which the device comes into contact; and
    an expandable cage disposed around the balloon, the expandable cage including at least a first elongated member, a second elongated member, and a collar adjacent proximal ends of the first and second elongated members, the first and second elongated members being spaced entirely apart from one another via a gap in the expandable cage, the first elongated member having a first length and the second elongated member having a second length, the central longitudinal axis lying in a first plane that extends through the first elongated member along the first length, and the central longitudinal axis lying in a second plane that extends through the second elongated member along the second length, the first and second elongated members each including an outer surface, an inner surface, and two side surfaces extending between the outer and inner surfaces, the outer surface, the inner surface, and the two side surfaces each having a minimum dimension transverse to the central longitudinal axis, the minimum dimensions of the outer and inner surfaces being at least two times greater than the minimum dimensions of the side surfaces, and the outer and inner surfaces each having a length and including flattened portions along majorities of the lengths thereof, the expandable cage being configured to expand with the expandable balloon, during expansion of the balloon to the expanded position, in a direction transverse to the central longitudinal axis when the outer surface of the expandable balloon applies a force to the inner surfaces of the first and second elongated members.

11. A device as recited in claim 10, further comprising at least a second electrode, the at least the second electrode being disposed within the thickness of the wall.

12. A method for destroying one of tissue and nerves at a surgical site comprising:

utilizing a device comprising:
- a cannula extending between a proximal end and a distal end, the cannula including at least an outer surface and an inner surface;
- a balloon disposed at the distal end of the cannula, the balloon having an unexpanded position, an expanded position, being configured to receive an inflation material, and including at least a wall, the wall of the balloon defining a thickness, an outer surface and an inner surface, the inner surface of the balloon defining a cavity, the cannula and the balloon defining a central longitudinal axis;
- at least a first electrode disposed on the inner surface of the balloon, the at least the first electrode configured for emitting RF signals;
- a cooling tube disposed within the thickness of the wall, the cooling tube being configured to attach to a liquid pumping device to circulate cooled liquid within the cooling tube so as to cool the inflation material, thereby cooling surrounding tissue with which the device comes into contact; and
- an expandable cage disposed around the balloon, the expandable cage including at least a first elongated member, a second elongated member, and a collar adjacent proximal ends of the first and second elongated members, the first and second elongated members being spaced entirely apart from one another via a gap in the expandable cage, the first elongated member having a first length and the second elongated member having a second length, the central longitudinal axis lying in a first plane that extends through the first elongated member along the first length, and the central longitudinal axis lying in a second plane that extends through the second elongated member along the second length, the first and second elongated members each including an outer surface, an inner surface, and two side surfaces extending between the outer and inner surfaces, the outer surface, the inner surface, and the two side surfaces each having a minimum dimension transverse to the central longitudinal axis, the minimum dimensions of the outer and inner surfaces being at least two times greater than the minimum dimensions of the side surfaces, and the outer and inner surfaces each having a length and including flattened portions along majorities of the lengths thereof, the expandable cage being configured to expand with the balloon, during expansion of the balloon to the expanded position, in a direction transverse to the central longitudinal axis when the outer surface of the expandable balloon applies a force to the inner surfaces of the first and second elongated members;

creating an access path to the surgical site;

inserting the balloon and the cage into the surgical site;

inflating the balloon and the cage in the direction transverse to the central longitudinal axis; and emitting RF signals through the at least the first electrode to destroy the one of the tissue and the nerves at the surgical site.

13. A method as recited in claim 12, further including cooling surrounding tissue with which the device comes into contact by pumping cooling liquid through the cooling tube.

* * * * *

UNITED STATES PATENT AND TRADEMARK OFFICE
CERTIFICATE OF CORRECTION

PATENT NO. : 9,861,431 B2
APPLICATION NO. : 13/799200
DATED : January 9, 2018
INVENTOR(S) : Goshayeshgar Page 1 of 1

It is certified that error appears in the above-identified patent and that said Letters Patent is hereby corrected as shown below:

On the Title Page

In Item (71), under "Applicant", in Column 1, Line 1, delete "KYPHON SARL, Neuchatel" and insert -- KYPHON SÀRL, Neuchâtel --, therefor.

In the Specification

In Column 2, Line 31, delete "disclosure; and" and insert -- disclosure. --, therefor.

In Column 6, Line 52, delete "nerves," and insert -- nerves. --, therefor.

In Column 6, Line 53, delete "electrode 50," and insert -- electrode 50 --, therefor.

In Column 7, Lines 3-4, delete "directionally if" and insert -- directionally. If --, therefor.

In Column 8, Line 16, delete "can he" and insert -- can be --, therefor.

In Column 8, Line 17, delete "markers," and insert -- markers. --, therefor.

In Column 8, Line 18, delete "bailoon" and insert -- balloon --, therefor.

Signed and Sealed this
Twelfth Day of June, 2018

Andrei Iancu
*Director of the United States Patent and Trademark Office*